United States Patent [19]

VandenBerg

[11] Patent Number: Plant 6,903

[45] Date of Patent: Jul. 4, 1989

[54] CHRYSANTHEMUM PLANT NAMED PALETO

[75] Inventor: Cornelis P. VandenBerg, Salinas, Calif.

[73] Assignee: Yoder Brothers, Inc., Ashtabula, Ohio

[21] Appl. No.: 187,655

[22] Filed: Apr. 28, 1988

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Paleto particularly characterized by its flat capitulum form; daisy capitulum type; orange-bronze ray floret color; diameter across face of capitulum of up to 8 cm at maturity; uniform eight week photoperiodic flowering response to short days; peduncle length ranging from 10 to 20 cm on open, terminal sprays; medium plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Paleto.

Paleto, identified as 82J22009, was originated from a cross made by Cornelis P. VandenBerg in a controlled breeding program in Salinas, Calif. in 1982.

The female parent of Paleto was the cultivar Mellow, disclosed in U.S. Plant Pat. No. 5,166. The male parent of Paleto was the cultivar Dragon, disclosed in U.S. Plant Pat. No. 4,696. Paleto was discovered and selected as one flowering plant within the progeny of the stated cross by Cornelis P. VandenBerg in June 1982 in a controlled environment in Salinas, Calif.

The first act of asexual reproduction of Paleto was accomplished when vegetative cuttings were taken from the initial selection in August 1982 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Paleto are firmly fixed and are retained through successive generations of asexual reproduction.

Paleto has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Paleto, which, in combination, distinguish this Chrysanthemum as a new and distinct cultivar:

1. Flat capitulum form.
2. Daisy capitulum type.
3. Orange-bronze ray floret color.
4. Diameter across face of capitulum up to 8 cm at maturity.

5. Uniform eight week photoperiodic flowering response to short days.
6. Peduncle length ranging from 10 to 20 cm on open terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Paleto, with the colors being as nearly true as possible with illustrations of this type.

Sheet 1 is a color photograph of Paleto grown as a single stem cut spray mum.

Sheet 2 is a black and white photograph of three views of the inflorescence of Paleto.

Sheet 3 is a black and white photograph showing the upper and under sides of the leaves of Paleto at three stages of development (mature, intermediate and immature).

Of the commercial cultivars known to the inventor, the most similar in comparison to Paleto is Amber, disclosed in U.S. Plant Pat. No. 3,969. Reference is made to Chart A, which compares certain characteristics of Paleto to the same characteristics of Amber.

Similar traits are ray floret color, capitulum form and type, capitulum diameter and plant height. Paleto is distinguished from Amber by its longer peduncles, shorter flowering response period, and superior low temperature tolerance.

In the following description, color references are made to The Royal Horticultural Society Colour Chart. The exact ray floret color of Paleto is not represented in The Royal Horticultural Society Colour Chart, and the values given are those closest to the actual color of Paleto. The color values were determined on plant material grown in Salinas, Calif. on Oct. 14, 1987.

Classification:

*Botanical.—Dendranthema grandiflora,* cv Paleto.

*Commercial.*—Daisy cut spray mum.

INFLORESCENCE

A. Capitulum:

*Form.*—Flat.

*Type.*—Daisy.

*Diameter across face.*—Up to 8 cm at maturity.

B. Corolla of ray florets:

*Color (general tonality from a distance of three meters).*—Orange-bronze.

*Color (upper surface).*—Closest to 163A to 163B, slightly tinged with 167A.

*Color (under surface).*—Closest to 163B.

*Shape.*—Flat; oblong.

C. Corolla of disc florets:

*Color (mature).*—12A to 12B.

*Color (immature).*—Closest to 144B.

D. Reproductive organs:

*Androecium.*—Present on disc florets only; abundant pollen.

*Gynoecium.*—Present on both ray and disc florets.

PLANT

A. General appearance:

*Height.*—Medium; 90 to 100 cm as a single stem cut mum with two long day weeks prior to short days.

B. Foliage:

*Color (upper surface).*—147A.

*Color (under surface).*—147B.

*Shape.*—Lobed and slightly serrated.

CHART A

COMPARISON OF PALETO AND AMBER

| | Paleto | Amber |
|---|---|---|
| Ray floret color | Orange bronze | Orange bronze |
| Capitulum form and type | Flat<br>Daisy | Flat<br>Daisy |
| Spray formation | Terminal<br>10 to 20 cm peduncles | Terminal<br>8 to 15 cm peduncles |
| Diameter across face of capitulum | Up to 8 cm | Up to 8 cm |
| Plant height | Medium | Medium |
| Flowering response period | 8 weeks | 9 weeks |
| Low temperature tolerance | Excellent | Poor |

COMPARISONS MADE OF PLANTS GROWN AS SINGLE STEM SPRAY CUT MUMS IN SALINAS, CALIFORNIA

I claim:

1. A new and distinct Chrysanthemum plant named Paleto, as described and illustrated, and parts thereof.

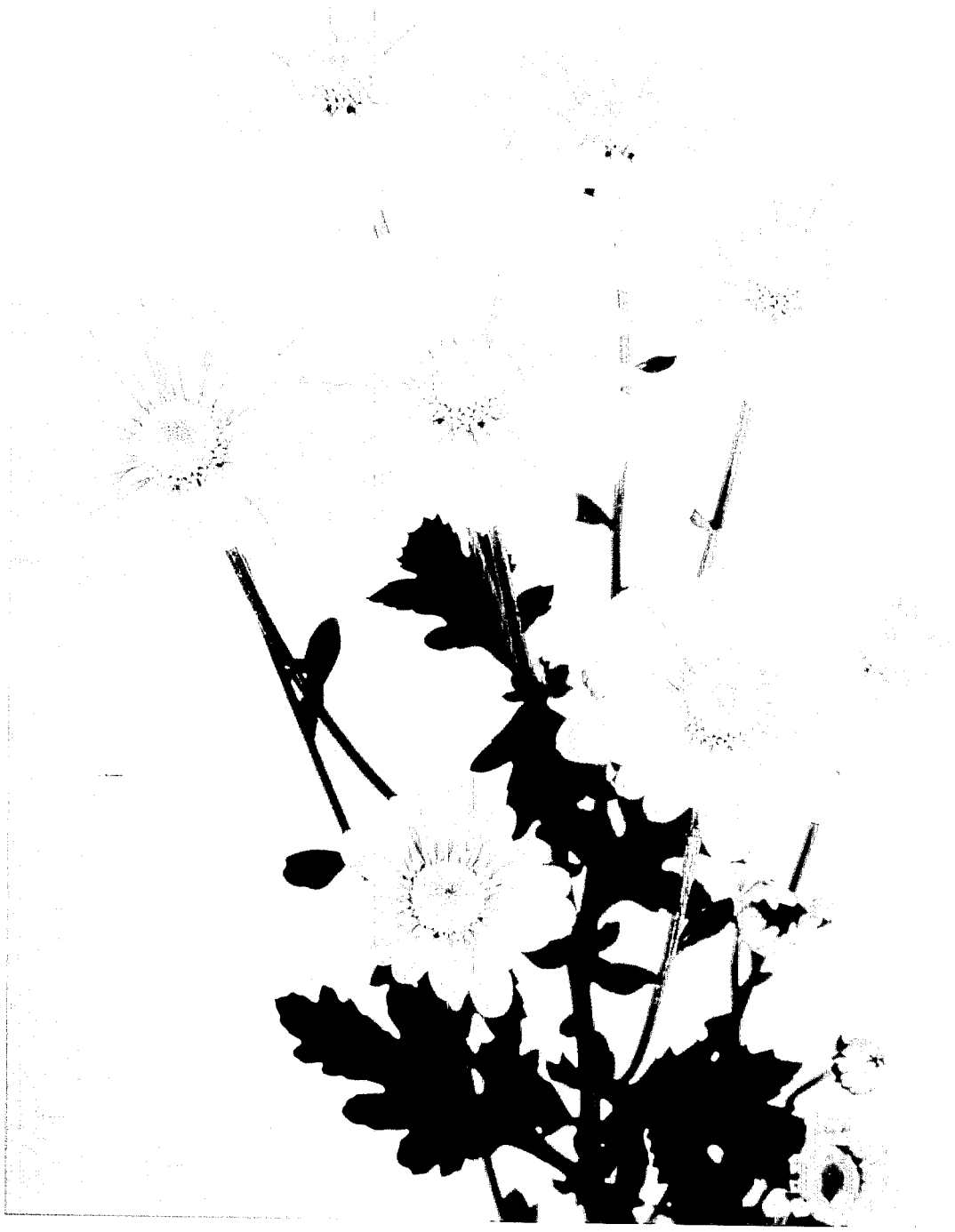

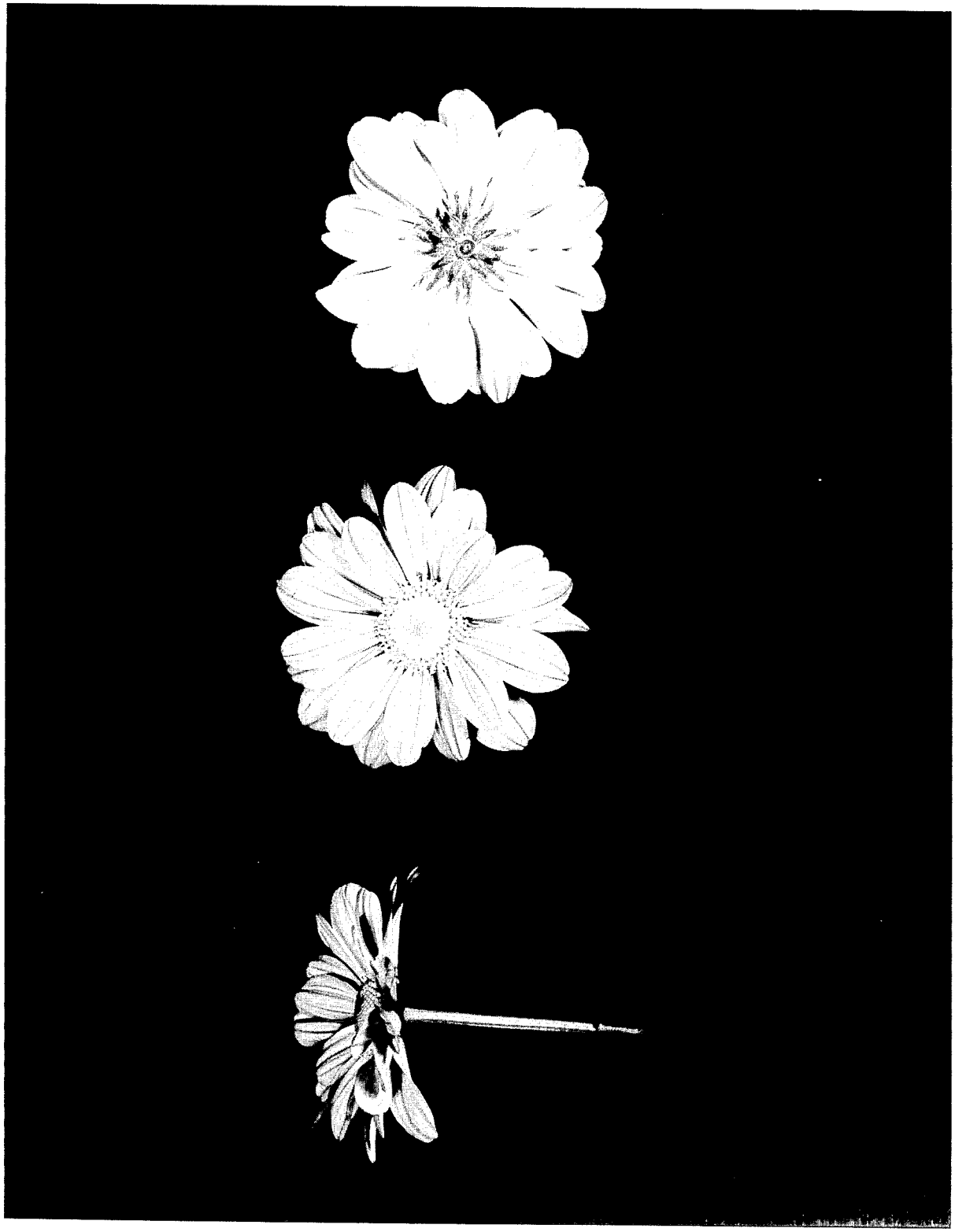

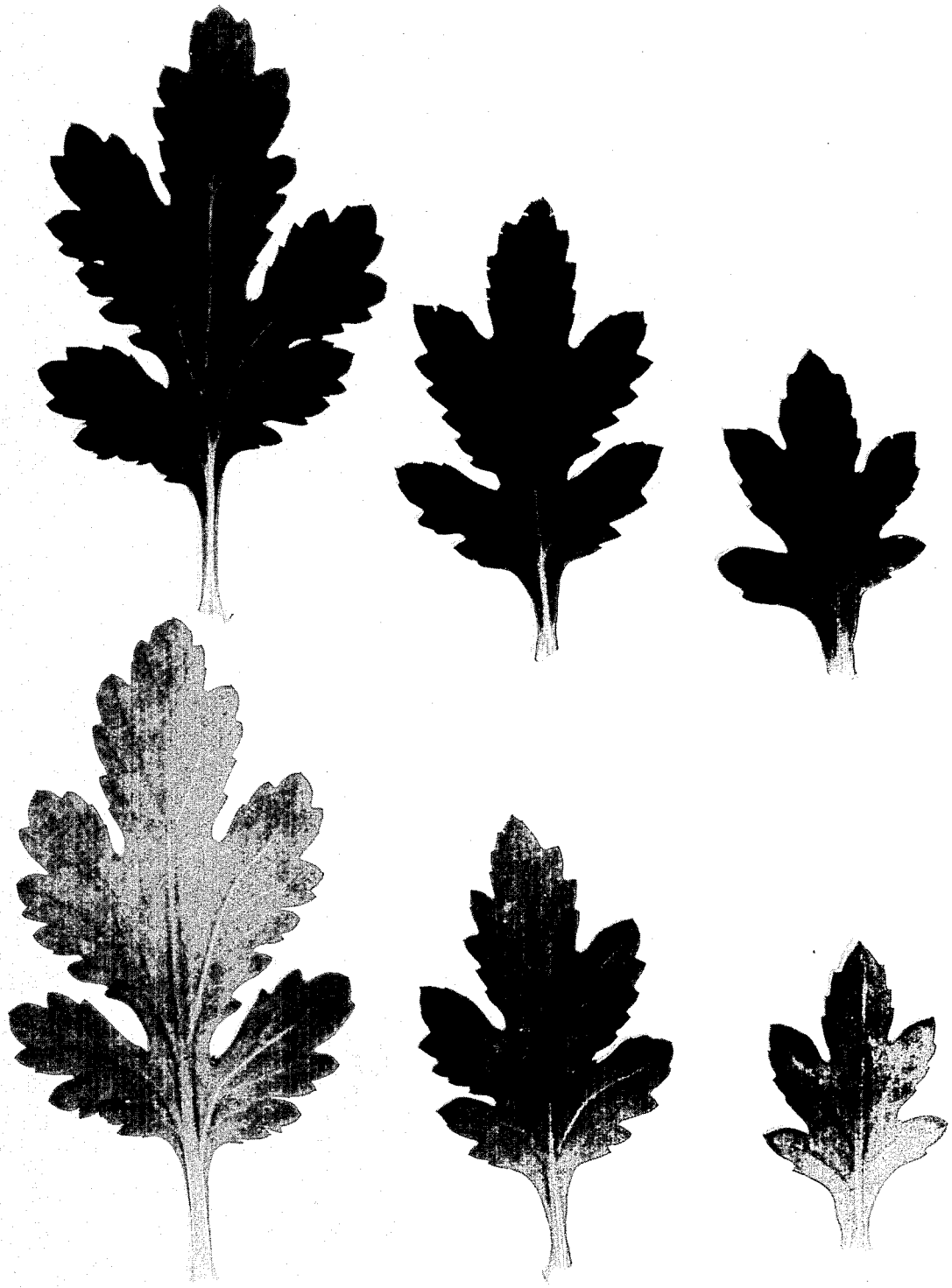

* * * * *